(12) United States Patent
Fernández et al.

(10) Patent No.: US 8,273,730 B2
(45) Date of Patent: Sep. 25, 2012

(54) USE OF ESTRIOL IN LOW DOSES

(75) Inventors: Álvaro Acebrón Fernández, Madrid (ES); Dolores Blanco Lousame, Madrid (ES); Jaime Moscoso Del Prado, Madrid (ES)

(73) Assignee: Italfarmaco, SA, Madrid (ES)

( * ) Notice: Subject to any disclaimer, the term of this patent is extended or adjusted under 35 U.S.C. 154(b) by 0 days.

(21) Appl. No.: 12/440,638

(22) PCT Filed: Jun. 25, 2008

(86) PCT No.: PCT/ES2008/000450
§ 371 (c)(1),
(2), (4) Date: Jul. 17, 2009

(87) PCT Pub. No.: WO2009/000954
PCT Pub. Date: Dec. 31, 2008

(65) Prior Publication Data
US 2009/0318401 A1    Dec. 24, 2009

(30) Foreign Application Priority Data
Jun. 25, 2007  (ES) .................................. 200701755

(51) Int. Cl.
A61K 31/56     (2006.01)
(52) U.S. Cl. ...................................................... 514/182
(58) Field of Classification Search ................... 514/182
See application file for complete search history.

(56) References Cited

U.S. PATENT DOCUMENTS

| | | |
|---|---|---|
| 3,159,543 A | 12/1964 | Ercoli |
| 5,942,243 A | 8/1999 | Shah |
| 2006/0240111 A1 | 10/2006 | Fernández |

FOREIGN PATENT DOCUMENTS

| | | |
|---|---|---|
| EP | 1325752 A2 | 7/2003 |
| EP | 1 652 535 A1 | 5/2006 |
| WO | 9507699 | 3/1995 |
| WO | 9629056 | 9/1996 |
| WO | WO 2007/085020 A2 | 7/2007 |

OTHER PUBLICATIONS

Puck et al., "Die Wirkung des Oestriol and Corpus uteri, Cervix uteri und Vagina der Frau", Deutsche Medizinische Wochenschrift, Georg Thieme, Stuttgart, DE, vol. 82, No. 44, Jan. 1, 1957, pp. 1864-1874.
Supplementary European Search Report for EP 08787631.4 / PCT/ES2008/000450, dated May 21, 2010.
Barensten et al., "Continuous low dose estradiol released from a vaginal ring versus estriol vaginal cream for urogenital atrophy," European Journal of Obstetrics & Gynecology (1997) vol. 71, pp. 73-80.
Gerbaldo et al, "Endometrial morphology after 12 months of vaginal oestriol therapy in post-menopausal women," Maturitas (1991) vol. 13, pp. 269-274.
Palacios et al., "Low-dose, vaginally administered estrogens may enhance local benefits of systemic therapy in the treatment of urogenital atrophy in postmenopausal women on hormone therapy," Maturitas (2005) vol. 50, pp. 98-104.
Pinkerton et al., "Alternatives to the Use of Estrogen in Postmenopausal Women," Endocrine Reviews (1999) vol. 20 (3): pp. 308-320.
SPC Ovestation Cream patient information leaflet (PIL), 2008.

*Primary Examiner* — San-Ming Hui
(74) *Attorney, Agent, or Firm* — Hoffmann & Baron, LLP

(57) ABSTRACT

The invention relates to the use of low doses of estriol by vaginal route for treatment and/or prevention of urogenital atrophy due to estrogen deficit in women.

8 Claims, No Drawings

USE OF ESTRIOL IN LOW DOSES

CROSS-REFERENCE TO RELATED APPLICATIONS

This application is a National Stage of International Application No. PCT/ES2008/000450, filed Jun. 25, 2008, which claims priority of Spanish Application No. P200701755, filed Jun. 25, 2007, the contents of all of which are incorporated by reference herein in their entirety.

FIELD OF THE INVENTION

This invention relates to the use of low doses of estriol by vaginal route in the prevention and/or the treatment of urogenital atrophy due to estrogen deficit in women.

STATE OF THE ART

The climacteric is considered as a transitory phase in the life of a woman, located between the reproductive stage and the non-reproductive stage. During the climacteric there is a progressive reduction in the production of estrogens by the ovaries which is usually accompanied by a series of signs, symptoms and pathologies.

The main sign of this transition is the disappearance of menstruation (menopause) and the onset of multiple hormonal and psychic symptoms, vasomotor disorders (hot flashes and sweating) and genitourinary atrophy being the most common.

With the progressive reduction in estrogens in peri- and post-menopause there is a gradual reduction in the vaginal, urethral and vesical mucosa. When this atrophy becomes more marked, genital symptoms—vaginal burning and itching, atrophic vaginitis, dyspareunia and traumatic bleeding—and urological symptoms—repeated infections, dysuria and urinary incontinence—can increase. The hormonal deficit furthermore triggers a reduction in the support tissue which can cause prolapses and stress urinary incontinence.

Although urogenital atrophy is a natural consequence of the climacteric and menopause, the associated disorders frequently affect the quality of life of the woman, it is therefore important for doctors to quickly detect its presence and indicate a treatment.

The estrogen deficit not only occurs in the climacteric but also in other situations—such as the postpartum period—, urogenital atrophies also occurring which could be treated.

Hormone replacement therapy with estrogens is applied seeking to correct or reduce the consequences of the hormonal deficiency, and causes beneficial effects on the vasomotor and urogenital symptoms, reduces the loss of bone mass and the cardiovascular risk, but also increases the risk of suffering from certain types of cancer, particularly breast or endometrial cancer, and other pathologies, for example thromboembolism and hypertension.

Due to these associated risks, conventional protocols cause concern, leading doctors and patients to continuously demand less toxic hormone replacement proposals.

In the case of urogenital atrophy, the systematic treatment of the symptoms by means of hormone replacement therapy by oral route is not always necessary. An alternative is the administration of estrogens by vaginal route. However, this route is not risk-free since locally administered estrogen hormones could favor an unwanted endometrial proliferation and this hyperplasia, in the event of being considerable, could degenerate into hormone-dependent cancer.

Estriol is one of the estrogens used in the treatment of urogenital atrophy, particularly by vaginal route.

Currently marketed estriol formulations are designed for the vaginal administration of a dose of 0.5 mg/day (500 μg/day) for the first 2-3 weeks of treatment, followed by a dose of 0.5 mg 2 or 3 times/week. This dose is the one considered necessary so that the topical administration has its effect. However, these levels involve a risk of endometrial hyperplasia when administered in a prolonged manner over time, and therefore the administration is not carried out continuously. It is generally recommended to not prolong the treatment beyond 2-3 months.

SUMMARY OF THE INVENTION

As was mentioned above, it is necessary to have regimens of vaginal administration of estriol for the prevention and/or the treatment of urogenital atrophy which provide both safety and efficacy and, consequently, are more accepted by doctors and patients, thus resulting in greater adherence to the treatment and better quality of life of the patients.

The inventors have surprisingly found that the administration of less than 500 micrograms (500 μg=0.5 mg) of estriol a day allows achieving these objectives, reversing urogenital atrophy in women without causing endometrial hyperplasia.

These low doses of estriol are effective and safe regardless of the type of formulation which is used, and allow prolonging the treatment without risks for the patient. In fact, it would allow a daily administration of the product for more than 3 weeks.

The present invention therefore relates to the use of estriol in the preparation of a pharmaceutical composition for vaginal administration for the prevention and/or the treatment of urogenital atrophy due to estrogen deficit in women, in which said composition is administered such that the patient receives a dose of estriol less than 0.5 mg/day, the treatment being able to be prolonged without risks.

DETAILED DESCRIPTION OF THE INVENTION

The inventors have found that a topical formulation containing estriol as an active ingredient can be administered at especially low doses and even so be effective in the treatment of urogenital atrophy in women.

Very surprisingly, it has been seen that doses even between 10 and 250 times smaller than the usual dose reverse the vaginal atrophy condition, even without needing additional therapy. Furthermore, these low doses significantly reduce the risk due to the treatment with estrogens.

In one aspect, the invention relates to the use of estriol in the preparation of a pharmaceutical composition for vaginal administration for the prevention and/or the treatment of urogenital atrophy due to estrogen deficit in women in which said composition is administered such that the patient receives a dose of estriol less than 0.5 mg/day.

The pharmaceutical compositions used in the present invention can be any of those known to a person skilled in the art allowing the administration of doses less than 0.5 mg/day of estriol. It can be, for example, in solid form (capsules, tablets, etc.), semisolid form (gels, creams, etc.), liquid form or foam form. And it can contain any of the excipients known to a person skilled in the art.

An important aspect of the present invention is the especially low doses of estriol which can be used in the formulations defined in the invention, and which are effective for the treatment of urogenital atrophy due to estrogen deficit.

In a particular embodiment of the present invention, estriol is administered in doses less than or equal to 0.3 mg/day for the prevention and/or the treatment of urogenital atrophy due to estrogen deficit.

Another even more preferred embodiment relates to the use of estriol in doses less than or equal to 0.1 mg/day.

Another particularly preferred embodiment relates to the use of estriol in doses between 0.002 and 0.05 mg/day (2 and 50 µg/day).

Another particularly preferred embodiment relates to the use of estriol in doses between 0.02 and 0.05 mg/day (20 and 50 µg/day).

Surprisingly, when using estriol in such low doses the product can be administered daily and for periods prolonged over time without there being adverse effects. Due to the high safety of the regimen of administration of estriol of the present invention, the prevention or the treatment of urogenital atrophy could be maintained without interruptions for a long time, for example months or years.

In a particular embodiment of the invention, the formulation is administered in a daily regimen for at least 3 weeks. In other embodiments it can be administered daily for at least 30 days, at least 60 days, at least 90 days, at least 6 months or at least 1 year. In these cases, it is preferably not necessary to interrupt the treatment.

In other embodiments the formulation could be administered in a regimen of once every two days, once every three days or once a week for at least 3 weeks, at least 30 days, at least 60 days, at least 90 days, at least 6 months or at least 1 year.

Several illustrative examples of the invention are described below. In no case must they be considered as limiting for the interpretation of the claims.

EXAMPLES

The efficacy of the use of low doses of estriol in the treatment of urogenital atrophy is shown through the following in vivo assays.

Assay I

Formulations

Two formulations were tested in this study, each of them containing 0.005% (w/w) of estriol.

To dissolve the active ingredient, a stock solution of estriol in glycerin was prepared. To that end, 25 mg of micronized estriol were added to 50 g of vegetable glycerin, it was stirred for 1 hour and the complete dissolution of estriol was verified.

To prepare the formulation in cream (Formulation 1), on one hand 20 g of Neo PCL o/w self-emulsifying base in an external aqueous phase were heated at 75° C. under magnetic stirring, whereas on the other hand 40 mg of Bronopol were dissolved in 70 ml of purified water at 75° C. The bronopol solution (aqueous, w) was gradually added on the self-emulsifying base (oily, o) and, under continuous stirring, the temperature was reduced until reaching 30° C. Without stopping the stirring, 10 grams of the previously prepared solution of estriol in glycerin were added, to obtain a 0.005% estriol formulation with the following composition:

| Component | Amount |
|---|---|
| Neo PCL o/w self-emulsifying base | 20 g |
| Bronopol | 40 mg |
| Purified water | 70 ml |
| Glycerin | 10 g |
| Micronized estriol | 5 mg |

To prepare the formulation in gel (Formulation 2), 40 mg of Bronopol were dissolved in 88 ml of purified water and 2 g of Natrosol were slowly added under continuous stirring. Finally, without stopping the stirring, 10 grams of the solution of estriol in glycerin were added, to obtain a 0.005% estriol formulation with the following composition:

| Component | Amount |
|---|---|
| Natrosol | 2 g |
| Bronopol | 40 mg |
| Purified water | 88 ml |
| Glycerin | 10 g |
| Micronized estriol | 5 mg |

Assessment of the Effect on Vaginal Atrophy

In this study a total of 8 female ovariectomized Wistar Han rats were used, which were randomly distributed into 2 groups with 4 animals each. Group A was treated with Formulation 1 whereas Group B was treated with Formulation 2.

After 18 days had elapsed from the reception of the ovariectomized animals, several vaginal smears were periodically performed in each rat, until the menopausal condition (particularly vaginal atrophy) was verified in all the rats, determining the maturation index of the vaginal epithelium.

Once the treatment had started, Formulations 1 (0.005% estriol cream) and 2 (0.005% estriol gel) were administered to experimental Group A and B, respectively, once a day for 5 days. The administration was carried out by vaginal route, in an amount of 5.8 mg of formulation/animal (corresponding to 0.29 µg of estriol/animal), using a positive displacement multipipette equipped with a special tip.

For the calculation of the dose to be administered to each animal, an average weight of 60 kg for women and of 350 g for rats was considered, whereby 0.29 µg of estriol were administered to each rat to assess the effect that the administration of 0.05 mg of estriol would have in a woman.

A vaginal smear was performed in each rat the first day before the administration, and another smear was performed when 8 hours had elapsed after the administration of day 5. The smears were performed by means of the vaginal lavage technique and were fixed and stained with the Papanicolau technique.

The effect of the treatment with each of the formulations was assessed by means of the appearance of cornified cells, the determination of the maturation index of the vaginal epithelium and the evaluation of the overall trophism.

The results obtained are shown in the following tables.

| | Day 0 | | | | | |
|---|---|---|---|---|---|---|
| Animal | MI | | | | Cornified | Overall |
| code | B | I | C | C − B | cells | trophism |
| A1 | 90 | 10 | 0 | −90 | N | A |
| A2 | 90 | 10 | 0 | −90 | N | A |
| A3 | 100 | 0 | 0 | −100 | N | A |
| A4 | 90 | 10 | 0 | −90 | N | A |

-continued

Day 0

| Animal code | MI B | MI I | MI C | MI C – B | Cornified cells | Overall trophism |
|---|---|---|---|---|---|---|
| B1 | 90 | 10 | 0 | −90 | N | A |
| B2 | 90 | 10 | 0 | −90 | N | A |
| B3 | 90 | 10 | 0 | −90 | N | A |
| B4 | 90 | 10 | 0 | −90 | N | A |

Day 5

| Animal code | MI B | MI I | MI C | MI C – B | Cornified cells | Overall trophism |
|---|---|---|---|---|---|---|
| A1 | 10 | 30 | 60 | 50 | Y | B |
| A2 | 10 | 30 | 60 | 50 | Y | B |
| A3 | 30 | 50 | 20 | −10 | Y | M |
| A4 | 10 | 30 | 60 | 50 | Y | B |
| B1 | 0 | 30 | 70 | 70 | Y | B |
| B2 | 0 | 30 | 70 | 70 | Y | B |
| B3 | 10 | 30 | 60 | 50 | Y | B |
| B4 | 10 | 30 | 60 | 50 | Y | B |

| | | |
|---|---|---|
| Maturation index | B | % basal/parabasal cells |
| | I | % intermediate cells |
| | C | % cornified cells |
| | C-B | % cornified cells - % basal/parabasal cells |
| Presence of cornified cells | N | No |
| | Y | Yes |
| Overall trophism | A | Atrophic |
| | H | Hypotrophic |
| | M | Intermediate trophism |
| | B | Good trophism |

The results demonstrate that the administration of a dose of estriol 10 times less than the dose usually used today reverses the vaginal atrophy condition in the rats of both groups, the presence of cornified and intermediate cells and a maturation index corresponding to eutrophic endometria being obtained after the treatment.

It can therefore be concluded that the regimen of administration proposed in the present invention will allow obtaining a therapeutic efficacy similar to that used currently but with greater safety.

Assay II

Two formulations in gel were tested in this study, one containing 0.002% and another 0.0002% (w/w) of estriol with the following composition.

| | |
|---|---|
| Estriol | 0.002% or 0.0002% |
| Carbopol 971P | 0.5% |
| Polycarbophil AA-1 | 1.5% |
| Glycerin | 10% |
| Methylparaben | 0.15% |
| Propylparaben | 0.05% |
| 37% HCl | q.s. pH 2.5-3.5 |
| 10% KOH | q.s. pH 4.5 |
| Water | q.s. 100% |

Assessment of the Effect on Vaginal Atrophy

Adult female ovariectomised Wistar rats housed in 255×405×197 mm polycarbonate E type cages, with beds of sawdust or the like, are used for this assay.

They are distributed into groups of 5 animals in each cage, chosen randomly, and they will be housed in animal housing units in controlled conditions of temperature (22±2° C.), photoperiod (12/12 h light/darkness), air pressure, number of renewals and relative humidity (40-60%).

They will be given a standard diet for rats, feed in pellets, supplied by Harlan Ibérica S. L. and they are allowed ad libitum access to drinking water (drinkable water for public consumption).

Five experimental groups with five animals each are used in the study. The substances to be assayed are three pharmaceutical formulations based on estriol and a placebo:
Group A: Control (Simulation)
Group B: treated with Placebo Gel
Group C: treated with 0.0002% Gel
Group D: treated with 0.002% Gel
Group E: treated with Reference Substance (0.1% Ovestinon)

For the calculation of the amount of the assay substances to be administered to each animal, a dosage in humans of 1 g of gel a day was considered.

Taking 60 Kg for women and 350 g for rats as an average weight.
60 Kg=1 g gel
350 g rat=5.8 mg gel In the case of the reference substance (0.1% Ovestinon), the dosage in humans is 0.5 g a day.

Taking 60 Kg for women and 350 g for rats as an average weight.
60 Kg=0.5 g cream
350 g rat=2.9 mg cream 5.8 mg of the corresponding assay substance will thus be administered to each animal of Groups B, C and D, whereas the animals of group E will receive 2.9 mg of the reference substance.

0.0002%/0.002% Gels=0.0002 g/0.002 g of estriol in 100 g of gel
0.002 mg/0.02 mg of estriol in 1 g of gel
0.1% Ovestinon=0.1 g of estriol in 100 g of cream
0.0005 g of estriol in 0.5 g of cream Therefore, the equivalent of active ingredient administered to each group is:
Group A: Control=0 μg estriol
Group B: Placebo=0 μg estriol
Group C: 0.0002% Gel=0.01 μg estriol: DOSE 1
Group D: 0.002% Gel=0.1 μg estriol: DOSE 2
Group E: 0.1% Ovestinon=2.9 μg estriol: DOSE 3

A control group is included in which vaginal administration is simulated to be able to determine the contribution of a possible "mechanical" effect on the observed trophic response.

The study consists of four phases:
The first phase lasts 15 days and involves the daily treatment of the animals.
The second phase lasts 15 days and involves the treatment of the animals twice a week (all the groups).
The third phase lasts 7 days and involves the treatment of the animals once a week (all the groups).
The third phase lasts 15 days and does not involve treatment.

Before the first administration (24 h) of the assay and reference substances, a vaginal smear is performed in each rat to verify its menopausal condition (vaginal atrophy), determining the maturation index of the vaginal epithelium.

To that end, the vaginal smears are performed by means of the lavage technique and are fixed with a water-soluble fixing spray for cytodiagnosis and stained according to the Papanicolau technique for the evaluation of the maturation index.

The first dose of the corresponding formulation is then administered to each treatment group. This administration is repeated once a day (every 24 hours) for 15 consecutive days.

After this period has elapsed, the dosage is changed to two weekly administrations in all the Groups A, B, C, D and E (Control, Placebo, 0.0002% Gel, 0.002% Gel and 0.1% Ovestinon) for 2 weeks.

When this period of 2 weeks ends, the dosage is once more changed to weekly administration in all the groups, for one week.

During the period of initial repeated administration (15 consecutive days), a vaginal smear is performed in all the animals daily until day 8 (inclusive), before the administration corresponding to that day. Another vaginal smear is also performed in all the animals on day 16, twenty-four hours after the last administration.

From this point onwards, vaginal smears are performed in all the animals every 3 days until the end of the study.

All the smears are fixed with a water-soluble fixing spray for cytodiagnosis and stained according to the Papanicolau technique for the evaluation of the maturation index The qualitative assessment of the trophic effect of the different treatments applied has been carried out according to the following scheme:
- A—Atrophic cytology
- H—Hypotrophic cytology
- M—Intermediate trophism cytology
- B—Cytology with good trophism To carry out the initial statistical analysis a numerical value has been given to each of these diagnoses:
- 0—A—Atrophic cytology
- 1—H—Hypotrophic cytology
- 2—M—Intermediate trophism cytology
- 3—B—Cytology with good trophism According to these premises the following results are obtained:

| Mean values of the qualitative analysis organized by type of treatment and duration | | | |
|---|---|---|---|
| CONTROL | Arithm. mean | PLACEBO | Arithm. mean |
| Baseline | 0.00 | Baseline | 0.00 |
| 2 d | 1.80 | 2 d | 1.80 |
| 3 d | 2.00 | 3 d | 2.00 |
| 4 d | 2.60 | 4 d | 2.40 |
| 5 d | 2.40 | 5 d | 2.00 |
| 6 d | 2.40 | 6 d | 3.00 |
| 7 d | 2.40 | 7 d | 2.80 |
| 8 d | 2.40 | 8 d | 2.00 |
| 16 d | 1.00 | 16 d | 1.40 |
| 19 d | 1.00 | 19 d | 1.40 |
| 22 d | 1.00 | 22 d | 1.00 |
| 25 d | 1.00 | 25 d | 1.20 |
| 28 d | 1.20 | 28 d | 1.40 |
| 31 d | 1.20 | 31 d | 1.20 |
| 34 d | 1.20 | 34 d | 1.00 |
| 37 d | 1.00 | 37 d | 0.40 |
| 40 d | 0.80 | 40 d | 0.40 |
| 43 d | 0.60 | 43 d | 0.20 |
| 46 d | 0.60 | 46 d | 0.80 |
| 49 d | 0.20 | 49 d | 0.20 |

| DOSE 1 | Arithm. mean | DOSE 2 | Arithm. mean | DOSE 3 | Arithm. mean |
|---|---|---|---|---|---|
| Baseline | 0.00 | Baseline | 0.00 | Baseline | 0.00 |
| 2 d | 2.00 | 2 d | 2.40 | 2 d | 2.80 |
| 3 d | 2.80 | 3 d | 3.00 | 3 d | 3.00 |
| 4 d | 3.00 | 4 d | 3.00 | 4 d | 3.00 |
| 5 d | 3.00 | 5 d | 3.00 | 5 d | 3.00 |
| 6 d | 3.00 | 6 d | 3.00 | 6 d | 3.00 |
| 7 d | 3.00 | 7 d | 3.00 | 7 d | 3.00 |
| 8 d | 3.00 | 8 d | 3.00 | 8 d | 3.00 |
| 16 d | 3.00 | 16 d | 3.00 | 16 d | 3.00 |
| 19 d | 2.40 | 19 d | 3.00 | 19 d | 2.80 |

| Individual values of the qualitative analysis | | | | | | | | | | | | | | | | | | | | | | |
|---|---|---|---|---|---|---|---|---|---|---|---|---|---|---|---|---|---|---|---|---|---|---|---|
| | RAT | | Baseline | 2 d | 3 d | 4 d | 5 d | 6 d | 7 d | 8 d | 16 d | 19 d | 22 d | 25 d | 28 d | 31 d | 34 d | 37 d | 40 d | 43 d | 46 d | 49 d |
| CONTROL | A | 1 | 0 | 2 | 2 | 2 | 3 | 3 | 2 | 3 | 1 | 1 | 1 | 1 | 2 | 1 | 2 | 1 | 1 | 0 | 1 | 0 |
| | A | 2 | 0 | 2 | 2 | 3 | 2 | 2 | 2 | 3 | 1 | 1 | 1 | 1 | 1 | 1 | 1 | 1 | 1 | 1 | 1 | 0 |
| | A | 3 | 0 | 1 | 2 | 3 | 2 | 3 | 3 | 2 | 1 | 1 | 1 | 1 | 1 | 1 | 1 | 1 | 0 | 0 | 0 | 0 |
| | A | 4 | 0 | 2 | 2 | 3 | 3 | 1 | 2 | 3 | 1 | 1 | 1 | 1 | 1 | 1 | 1 | 0 | 1 | 1 | 0 | 0 |
| | A | 5 | 0 | 2 | 2 | 2 | 2 | 3 | 3 | 2 | 1 | 1 | 1 | 1 | 2 | 1 | 1 | 1 | 1 | 0 | 1 | 1 |
| PLACEBO | B | 1 | 0 | 2 | 2 | 3 | 2 | 3 | 2 | 1 | 2 | 1 | 1 | 1 | 1 | 1 | 1 | 1 | 1 | 1 | 1 | 0 |
| | B | 2 | 0 | 1 | 2 | 2 | 2 | 3 | 3 | 1 | 1 | 2 | 1 | 1 | 1 | 1 | 1 | 0 | 0 | 0 | 1 | 0 |
| | B | 3 | 0 | 2 | 2 | 3 | 2 | 3 | 3 | 2 | 2 | 2 | 1 | 2 | 2 | 1 | 1 | 0 | 0 | 0 | 0 | 0 |
| | B | 4 | 0 | 2 | 2 | 2 | 2 | 3 | 3 | 3 | 1 | 1 | 1 | 1 | 1 | 1 | 1 | 1 | 1 | 0 | 1 | 0 |
| | B | 5 | 0 | 2 | 2 | 2 | 2 | 3 | 3 | 3 | 1 | 1 | 1 | 1 | 2 | 2 | 1 | 0 | 0 | 0 | 1 | 1 |
| DOSE 1 | C | 1 | 0 | 1 | 3 | 3 | 3 | 3 | 3 | 3 | 3 | 2 | 3 | 3 | 2 | 2 | 2 | 1 | 0 | 1 | 1 | 1 |
| | C | 2 | 0 | 2 | 3 | 3 | 3 | 3 | 3 | 3 | 3 | 2 | 2 | 2 | 2 | 2 | 2 | 2 | 1 | 1 | 1 | 1 |
| | C | 3 | 0 | 1 | 2 | 3 | 3 | 3 | 3 | 3 | 3 | 3 | 3 | 2 | 3 | 2 | 1 | 1 | 1 | 1 | 2 | 1 |
| | C | 4 | 0 | 3 | 3 | 3 | 3 | 3 | 3 | 3 | 3 | 2 | 3 | 2 | 3 | 2 | 1 | 2 | 1 | 1 | 2 | 1 |
| | C | 5 | 0 | 3 | 3 | 3 | 3 | 3 | 3 | 3 | 3 | 3 | 2 | 2 | 3 | 2 | 2 | 2 | 1 | 1 | 2 | 1 |
| DOSE 2 | D | 1 | 0 | 3 | 3 | 3 | 3 | 3 | 3 | 3 | 3 | 3 | 3 | 3 | 3 | 3 | 2 | 3 | 1 | 1 | 1 | 1 |
| | D | 2 | 0 | 2 | 3 | 3 | 3 | 3 | 3 | 3 | 3 | 3 | 3 | 3 | 3 | 2 | 3 | 2 | 1 | 1 | 1 | 1 |
| | D | 3 | 0 | 2 | 3 | 3 | 3 | 3 | 3 | 3 | 3 | 3 | 3 | 3 | 3 | 3 | 1 | 0 | 0 | 0 | 1 | 1 |
| | D | 4 | 0 | 2 | 3 | 3 | 3 | 3 | 3 | 3 | 3 | 3 | 3 | 3 | 3 | 2 | 3 | 2 | 1 | 1 | 2 | 2 |
| | D | 5 | 0 | 3 | 3 | 3 | 3 | 3 | 3 | 3 | 3 | 3 | 3 | 3 | 3 | 3 | 3 | 3 | 3 | 3 | 3 | 3 |
| DOSE 3 | E | 1 | 0 | 3 | 3 | 3 | 3 | 3 | 3 | 3 | 3 | 3 | 3 | 3 | 3 | 2 | 3 | 2 | 2 | 2 | 2 | 2 |
| | E | 2 | 0 | 2 | 3 | 3 | 3 | 3 | 3 | 3 | 3 | 2 | 2 | 3 | 3 | 1 | 3 | 3 | 2 | 1 | 1 | 1 |
| | E | 3 | 0 | 3 | 3 | 3 | 3 | 3 | 3 | 3 | 3 | 3 | 3 | 3 | 3 | 2 | 3 | 2 | 1 | 1 | 1 | 1 |
| | E | 4 | 0 | 3 | 3 | 3 | 3 | 3 | 3 | 3 | 3 | 3 | 3 | 3 | 3 | 2 | 2 | 2 | 1 | 1 | 1 | 2 |
| | E | 5 | 0 | 3 | 3 | 3 | 3 | 3 | 3 | 3 | 3 | 3 | 2 | 3 | 3 | 2 | 2 | 2 | 1 | 2 | 2 | 2 |

-continued

| DOSE 1 | Arithm. mean | DOSE 2 | Arithm. mean | DOSE 3 | Arithm. mean |
|---|---|---|---|---|---|
| 22 d | 2.60 | 22 d | 3.00 | 22 d | 2.80 |
| 25 d | 2.20 | 25 d | 3.00 | 25 d | 2.60 |
| 28 d | 2.60 | 28 d | 3.00 | 28 d | 3.00 |
| 31 d | 2.00 | 31 d | 2.60 | 31 d | 2.60 |
| 34 d | 1.60 | 34 d | 2.80 | 34 d | 2.20 |
| 37 d | 1.60 | 37 d | 2.20 | 37 d | 2.60 |
| 40 d | 0.80 | 40 d | 1.20 | 40 d | 2.00 |
| 43 d | 1.00 | 43 d | 1.20 | 43 d | 1.20 |
| 46 d | 1.60 | 46 d | 1.60 | 46 d | 1.40 |
| 49 d | 1.00 | 49 d | 1.60 | 49 d | 1.60 |

Therefore, it can be observed that:

In the control (simulation) and placebo groups an intermediate trophic effect is observed between days 2 and 8, a good trophism being observed between days 4 and 7 (only on some days). This increase may have a contribution due to the mechanical effect of the actual cytological sample taking, just as the subsequent reduction can be a factor due to a "habituation" or desensitization to said mechanical effect as has been observed in previous studies (see Tables 8 and 9).

In the groups to which substances with estriol are administered (dose 1 (0.01 µg estriol), dose 2 (0.1 µg estriol), dose 3 (2.9 µg estriol), a good trophism is observed between days 2 and 37. From this period, it becomes hypotrophy, coinciding with the stop of the administration of the different assay and reference substances (day 36 was the last day of administration).

It is therefore very advantageous to have a formulation of very low doses of estriol making possible the administration for a prolonged time, preventing the periods of hypotrophy or urogenital atrophy and providing high safety to the patient.

The quantitative analysis has been carried out by using the cell maturation index (MI), attributing a percentage of the total of cells to the amount of basal/parabasal, intermediate and surface cells. (B/I/S)

To carry out the initial statistical analysis, for the purpose of assigning a numerical value to each sample, the following formula has been used:

VALUE=$(-1*B)+(0*I)+(1*S)$

A range of values from −100 (100% of basal/parabasal cells) to 100 (100% of surface cells) was obtained by means of this formula, a value less than −90 being considered as total atrophy, between −89 and −30 hypotrophy, between −29 and +20 intermediate trophism and greater than +20 good trophism.

According to these premises the following results are obtained:

| Individual values of the quantitative analysis | | | | | | | | | | | | | |
|---|---|---|---|---|---|---|---|---|---|---|---|---|---|
| | RAT | | Baseline | 2 d | 3 d | 4 d | 5 d | 6 d | 7 d | 8 d | 16 d | 19 d | 22 d |
| CONTROL | A | 1 | −90 | 0 | −10 | −10 | 30 | −30 | 10 | 50 | −50 | −70 | −50 |
| | A | 2 | −90 | 0 | 0 | 30 | 10 | 10 | 10 | 30 | −60 | −60 | −60 |
| | A | 3 | −90 | −50 | 0 | 30 | 10 | 30 | 30 | 10 | −60 | −60 | −30 |
| | A | 4 | −100 | −20 | −30 | 30 | 30 | −70 | 10 | 10 | −50 | −50 | −30 |
| | A | 5 | −90 | 0 | 0 | 10 | 10 | 30 | 30 | 10 | −60 | −30 | −30 |
| PLACEBO | B | 1 | −100 | 0 | 0 | 30 | −10 | 30 | −10 | −50 | 10 | −50 | −50 |
| | B | 2 | −100 | −50 | −30 | −30 | −30 | 30 | 30 | −50 | −50 | −10 | −50 |
| | B | 3 | −100 | 10 | 0 | 30 | −30 | 50 | 30 | 10 | −10 | 10 | −30 |
| | B | 4 | −90 | 10 | −10 | −10 | −10 | 30 | 30 | 30 | −50 | −60 | −60 |
| | B | 5 | −100 | −20 | 10 | 10 | −30 | 30 | 30 | 30 | −60 | −60 | −50 |
| DOSE 1 | C | 1 | −100 | −50 | 50 | 50 | 50 | 50 | 50 | 30 | 40 | −10 | 50 |
| | C | 2 | −90 | 10 | 30 | 30 | 50 | 50 | 50 | 50 | 50 | −10 | 0 |
| | C | 3 | −100 | −50 | 10 | 30 | 60 | 60 | 50 | 30 | 60 | 40 | 50 |
| | C | 4 | −90 | 50 | 50 | 50 | 50 | 50 | 50 | 50 | 50 | −10 | 40 |
| | C | 5 | −100 | 50 | 50 | 50 | 30 | 50 | 50 | 50 | 50 | 40 | 10 |
| DOSE 2 | D | 1 | −90 | 50 | 50 | 50 | 30 | 50 | 50 | 50 | 40 | 50 | 50 |
| | D | 2 | −100 | 10 | 30 | 50 | 50 | 50 | 50 | 50 | 60 | 40 | 50 |
| | D | 3 | −100 | 10 | 50 | 50 | 50 | 50 | 50 | 50 | 50 | 50 | 40 |
| | D | 4 | −90 | 10 | 30 | 30 | 50 | 50 | 50 | 50 | 40 | 40 | 40 |
| | D | 5 | −90 | 50 | 50 | 50 | 50 | 50 | 50 | 50 | 50 | 60 | 60 |
| DOSE 3 | E | 1 | −100 | 50 | 50 | 30 | 60 | 50 | 50 | 80 | 90 | 30 | 50 |
| | E | 2 | −90 | 10 | 50 | 50 | 60 | 50 | 50 | 60 | 90 | 10 | 50 |
| | E | 3 | −90 | 50 | 50 | 50 | 60 | 60 | 50 | 60 | 90 | 40 | 50 |
| | E | 4 | −100 | 50 | 50 | 50 | 70 | 80 | 50 | 80 | 90 | 40 | 50 |
| | E | 5 | −100 | 50 | 30 | 70 | 70 | 70 | 80 | 90 | 90 | 50 | 40 |
| | RAT | | 25 d | 28 d | 31 d | 34 d | 37 d | 40 d | 42 d | 45 d | 48 d | | |
| CONTROL | A | 1 | −70 | −10 | −50 | 0 | −70 | −70 | −90 | −60 | −90 | | |
| | A | 2 | −70 | −60 | −60 | −70 | −70 | −60 | −70 | −70 | −90 | | |
| | A | 3 | −70 | −70 | −60 | −70 | −70 | −70 | −90 | −90 | −90 | | |
| | A | 4 | −70 | −70 | −70 | −70 | −70 | −90 | −60 | −70 | −90 | | |
| | A | 5 | −70 | −50 | −10 | −60 | −70 | −70 | −90 | −90 | −70 | | |
| PLACEBO | B | 1 | −70 | −50 | −60 | −70 | −70 | −60 | −60 | −70 | −90 | | |
| | B | 2 | −70 | −70 | −50 | −70 | −90 | −90 | −90 | −70 | −90 | | |
| | B | 3 | −10 | −10 | −50 | −70 | −90 | −90 | −90 | −90 | −90 | | |
| | B | 4 | −60 | −70 | −70 | −70 | −70 | −70 | −90 | −60 | −90 | | |
| | B | 5 | −40 | −10 | −10 | −70 | −90 | −90 | −90 | −70 | −70 | | |
| DOSE 1 | C | 1 | 30 | −10 | −10 | −10 | −70 | −90 | −70 | −70 | −70 | | |
| | C | 2 | −10 | 10 | −10 | −10 | −10 | −70 | −70 | −50 | −50 | | |
| | C | 3 | 0 | 40 | −10 | −50 | −30 | −70 | −70 | −10 | −70 | | |
| | C | 4 | −10 | 50 | 10 | −50 | 10 | −70 | −70 | −10 | −50 | | |
| | C | 5 | −10 | 50 | −10 | −10 | 10 | −70 | −70 | −10 | −60 | | |

-continued

| Individual values of the quantitative analysis | | | | | | | | | | | |
|---|---|---|---|---|---|---|---|---|---|---|---|
| DOSE 2 | D | 1 | 50 | 40 | 50 | −10 | 30 | −70 | −60 | −70 | −70 |
| | D | 2 | 30 | 50 | −10 | 30 | −10 | −50 | −70 | −50 | −60 |
| | D | 3 | 30 | 30 | 30 | 30 | −60 | −90 | −90 | −60 | −60 |
| | D | 4 | 30 | 50 | −10 | 30 | −10 | −50 | −60 | 0 | −10 |
| | D | 5 | 60 | 50 | 50 | 50 | 50 | 30 | 30 | 50 | 50 |
| DOSE 3 | E | 1 | 50 | 60 | 60 | 10 | 30 | 0 | 10 | 0 | 10 |
| | E | 2 | 50 | 50 | −50 | 30 | 30 | 0 | −50 | −60 | −60 |
| | E | 3 | 30 | 30 | 30 | −10 | 30 | −10 | −60 | −60 | −60 |
| | E | 4 | −10 | 30 | 30 | −10 | −10 | −10 | −60 | −70 | −10 |
| | E | 5 | −10 | 60 | 60 | 10 | 10 | 10 | −50 | 10 | −10 |

| Mean values of the quantitative analysis organized by type of treatment and duration | | | |
|---|---|---|---|
| CONTROL | Arithm. mean | PLACEBO | Arithm. mean |
| Baseline | −92.00 | Baseline | −98.00 |
| 2 d | −14.00 | 2 d | −10.00 |
| 3 d | −8.00 | 3 d | −6.00 |
| 4 d | 18.00 | 4 d | 6.00 |
| 5 d | 18.00 | 5 d | −22.00 |
| 6 d | −6.00 | 6 d | 34.00 |
| 7 d | 18.00 | 7 d | 22.00 |
| 8 d | 22.00 | 8 d | −6.00 |
| 16 d | −56.00 | 16 d | −32.00 |
| 19 d | −54.00 | 19 d | −34.00 |
| 22 d | −40.00 | 22 d | −48.00 |
| 25 d | −70.00 | 25 d | −50.00 |
| 28 d | −52.00 | 28 d | −42.00 |
| 31 d | −50.00 | 31 d | −48.00 |
| 34 d | −54.00 | 34 d | −70.00 |
| 37 d | −70.00 | 37 d | −82.00 |
| 40 d | −72.00 | 40 d | −80.00 |
| 43 d | −76.00 | 43 d | −84.00 |
| 46 d | −76.00 | 46 d | −72.00 |
| 49 d | −86.00 | 49 d | −86.00 |

| DOSE 1 | Arithm. mean | DOSE 2 | Arithm. mean | DOSE 3 | Arithm. mean |
|---|---|---|---|---|---|
| Baseline | −96.00 | Baseline | −94.00 | Baseline | −96.00 |
| 2 d | 2.00 | 2 d | 26.00 | 2 d | 42.00 |
| 3 d | 38.00 | 3 d | 42.00 | 3 d | 46.00 |
| 4 d | 42.00 | 4 d | 46.00 | 4 d | 50.00 |
| 5 d | 48.00 | 5 d | 46.00 | 5 d | 64.00 |
| 6 d | 52.00 | 6 d | 50.00 | 6 d | 62.00 |
| 7 d | 50.00 | 7 d | 50.00 | 7 d | 56.00 |
| 8 d | 42.00 | 8 d | 50.00 | 8 d | 74.00 |
| 16 d | 50.00 | 16 d | 48.00 | 16 d | 90.00 |
| 19 d | 10.00 | 19 d | 48.00 | 19 d | 34.00 |
| 22 d | 30.00 | 22 d | 48.00 | 22 d | 48.00 |
| 25 d | 0.00 | 25 d | 40.00 | 25 d | 22.00 |
| 28 d | 28.00 | 28 d | 44.00 | 28 d | 46.00 |
| 31 d | −6.00 | 31 d | 22.00 | 31 d | 26.00 |
| 34 d | −26.00 | 34 d | 26.00 | 34 d | 6.00 |
| 37 d | −18.00 | 37 d | 0.00 | 37 d | 18.00 |
| 40 d | −74.00 | 40 d | −46.00 | 40 d | −2.00 |
| 43 d | −70.00 | 43 d | −50.00 | 43 d | −42.00 |
| 46 d | −30.00 | 46 d | −26.00 | 46 d | −36.00 |
| 49 d | −60.00 | 49 d | −30.00 | 49 d | −26.00 |

Therefore, it can be observed that:

The results, assessment and analysis are very similar to those obtained with the qualitative assessment.

In the control (simulation) and placebo groups an intermediate trophic effect was observed between days 2 and 8, a good trophism being observed between days 4 and 7, this is demonstrated with the appearance of intermediate cells and in some case surface cells. This effect is progressively reduced throughout the study.

In the dose 1 group (0.01 μg estriol), a good trophism with intermediate and surface cells is observed between treatment days 2 and 16, coinciding with the daily administration until day 15. Afterwards, a fluctuation between good trophism and intermediate trophism is observed, resulting in an intermediate trophism condition from day 37 of the study (day 36 was the last day of administration), reaching a hypotrophic condition from day 40.

The rest of the groups containing estriol (dose 2 (0.1 μg estriol) and dose 3 (2.9 μg estriol) have a similar behavior. A good trophism is observed between days 2 and 36. On day 37 for dose 3 there is good trophism whereas for dose 2 there is intermediate trophism. In dose 2 a hypotrophy condition is acquired one day sooner than for dose 3.

The invention claimed is:

1. A method for treating urogenital atrophy due to estrogen deficit in women comprising administering to a patient in need thereof a therapeutically effective amount of a pharmaceutical composition for vaginal administration, wherein said composition is administered such that the patient receives a dose of estriol between 0.002 and 0.3 mg/day; and wherein the administration is daily or in a regimen of once every two days, once every three days or once a week or twice a week, for at least 3 weeks.

2. A method according to claim 1, wherein the patient receives a dose of estriol less than or equal to 0.1 mg/day.

3. A method according to claim 1, wherein the patient receives a dose of estriol between 0.002 and 0.05 mg/day.

4. A method according to claim 1, wherein the patient receives a dose of estriol between 0.02 and 0.05 mg/day.

5. A method according to claim 1, wherein the administration is daily for at least 3 weeks.

6. A method according to claim 5, wherein the administration is for at least 30 days.

7. A method according to claim 5, wherein the administration is for at least 60 days.

8. A method according to claim 5, wherein the administration is for at least 90 days.

* * * * *